United States Patent
Della Valle et al.

(10) Patent No.: US 9,512,091 B2
(45) Date of Patent: Dec. 6, 2016

(54) COMPOSITIONS AND METHODS FOR THE MODULATION OF SPECIFIC AMIDASES FOR N-ACYLETHANOLAMINES FOR USE IN THE THERAPY OF INFLAMMATORY DISEASES

(75) Inventors: Francesco Della Valle, Milan (IT); Maria Federica Della Valle, Milan (IT); Gabriele Marcolongo, Milan (IT); Vincenzo Di Marzo, Milan (IT); Salvatore Cuzzocrea, Milan (IT)

(73) Assignee: Epitech Group S.r.l., Milan (IT)

( * ) Notice: Subject to any disclaimer, the term of this patent is extended or adjusted under 35 U.S.C. 154(b) by 0 days.

(21) Appl. No.: 14/378,185

(22) PCT Filed: Feb. 17, 2012

(86) PCT No.: PCT/IT2012/000050
§ 371 (c)(1),
(2), (4) Date: Oct. 15, 2014

(87) PCT Pub. No.: WO2013/121449
PCT Pub. Date: Aug. 22, 2013

(65) Prior Publication Data
US 2015/0057269 A1   Feb. 26, 2015

(51) Int. Cl.
| | |
|---|---|
| C07D 263/12 | (2006.01) |
| C07D 277/10 | (2006.01) |
| C07D 265/06 | (2006.01) |
| A61K 31/421 | (2006.01) |
| C07D 263/10 | (2006.01) |
| C07D 263/14 | (2006.01) |
| A61K 45/06 | (2006.01) |
| A61K 31/164 | (2006.01) |
| A61K 31/426 | (2006.01) |
| A61K 31/535 | (2006.01) |
| C07D 263/32 | (2006.01) |

(52) U.S. Cl.
CPC .......... *C07D 263/12* (2013.01); *A61K 31/164* (2013.01); *A61K 31/421* (2013.01); *A61K 31/426* (2013.01); *A61K 31/535* (2013.01); *A61K 45/06* (2013.01); *C07D 263/10* (2013.01); *C07D 263/14* (2013.01); *C07D 263/32* (2013.01); *C07D 265/06* (2013.01); *C07D 277/10* (2013.01)

(58) Field of Classification Search
CPC . C07D 263/32; C07D 265/06; C07D 263/12
See application file for complete search history.

(56) References Cited

U.S. PATENT DOCUMENTS

| | | |
|---|---|---|
| 3,920,567 A | 11/1975 | Miller |
| 4,224,172 A | 9/1980 | Schmitt et al. |
| 4,876,249 A | 10/1989 | Rajadhyaksha |
| 6,462,054 B1 | 10/2002 | Boger |
| 2005/0075380 A1 | 4/2005 | Msika et al. |
| 2009/0274637 A1 | 11/2009 | Msika et al. |

FOREIGN PATENT DOCUMENTS

| | | |
|---|---|---|
| EP | 0 238 210 A2 | 9/1987 |
| WO | WO 2009/154785 A2 | 12/2009 |
| WO | WO 2011/085216 A2 | 7/2011 |

OTHER PUBLICATIONS

Msika, et al. Document No. 145:460556, retrieved from CAPLUS; entered in STN on Nov. 2, 2006.*
Rajadhyaksha. Document No. 109:237052, retrieved from CAPLUS, entered in STN on Dec. 24, 1988.*
Jeronimo, et al. Document No. 156:476079, retreived from CAPLUS; 2011.*
Saito, et al. Document No. 151:339795, retrieved from CAPLUS; Sep. 9, 2009.*
Lin, et al. Document No. 130:177116, retrieved from CAPLUS; 1998.*
Cecil Textbook of Medicine, 20th edition (1996), vol. 2, pp. 2050-2057.J.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http:IIwww.cnn.com120031HEALTHIconditionsIO91241alzheimers.drug.aplindexhtml>.*

(Continued)

*Primary Examiner* — Shawquia Jackson
(74) *Attorney, Agent, or Firm* — Blank Rome LLP

(57) ABSTRACT

The present invention regards compositions and methods for the modulation of amidases capable of hydrolyzing N-acylethanolamines useable in the therapy of inflammatory diseases. In particular, the present invention regards a compound of general formula (I): enantiomers, diastereoisomers, racemes and mixtures, polymorphs, salts, solvates thereof, wherein: (a) R is a linear alkyl radical having 13 to 19 carbon atoms or alkenyl radical having 13 to 19 carbon atoms carrying a double bond; (b) X is O or S; (c) Y is a 2 or 3 carbon atom alkylene residue, optionally substituted with one or two groups equal or different from each other and selected from among the group consisting of: —$CH_3$, —$CH_2OH$, —$COOCH_3$, —COOH. Y may preferably be: —$CH_2$—$CH_2$—, —$CH_2$—$CH_2$—$CH_2$—, $CH(CH_3)$—$CH_2$—, —$CH_2$—$CH(CH_3)$—, —$CH_2$—$C(CH_3)_2$—, —$CH_2$—$CH(CH_2OH)$—, —$CH_2$—$C((CH_2OH)_2)$—, —CH=CH—, —$CH_2$—$CH(COOCH_3)$—, —$CH_2$—$CH(COOH)$—, for use as a medicine.

(I)

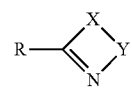

7 Claims, No Drawings

(56) References Cited

OTHER PUBLICATIONS

Vippagunta, et al. Advanced Drug Delivery Reviews 48 (2001) 3-26.*
Concise Encyclopedia Chemistry (1993) Walter de Gruyter Berlin New York.*
A. Jarrahian et al., "Structure-Activity Relationships Among N-Arachidonylethanolamine (Anandamide) Head Group Analogues for the Anandamide Transporter", Journal of Neurochemistry, vol. 74, No. 6, Jun. 2000, pp. 2597-2606.
Chemical Abstracts Service, Columbus, Ohio, May 25, 1985 XP002676573.
Chemical Abstracts Service, Columbus, Ohio, May 12, 1985 XP002676574.
Chemical Abstracts Service, Columbus, Ohio, Aug. 31, 1985 XP002676575.
Chemical Abstracts Service, Columbus, Ohio, Jul. 12, 1986 XP002676576.
Chemical Abstracts Service, Columbus, Ohio, Nov. 16, 1984 XP002676577.
Chemical Abstracts Service, Columbus, Ohio, Nov. 16, 1984 XP002676578.

* cited by examiner

COMPOSITIONS AND METHODS FOR THE MODULATION OF SPECIFIC AMIDASES FOR N-ACYLETHANOLAMINES FOR USE IN THE THERAPY OF INFLAMMATORY DISEASES

FIELD OF THE INVENTION

The present invention regards compositions and methods for the modulation of amidases capable of hydrolysing N-acylethanolamines useable for treating inflammatory diseases.

STATE OF THE ART

Palmitoylethanolamide (PEA), a lipid substance belonging to the family of N-acylethanolamine (NAE), is currently considered an important endogenous molecule capable of controlling the reactivity of the tissues and the related inflammatory and algic phenomena, both at innervated peripheral tissue level and at the central nervous, spinal and supra-spinal tissue level. Actually, PEA considerably reduces the neurogenic inflammation induced by substance P and it exerts an anti-inflammatory effect in many other forms of acute inflammation, such as dextran, formalin and carrageenan edema; passive skin anaphylaxis, TPA edema, DNFB dermatitis in mice and allergic dermatitis in dogs. Furthermore, it is also known that PEA exerts considerable anti-inflammatory effects even in chronic inflammation models, such as for example carrageenan granuloma. PEA also revealed to be active, both in the animal model and human pathology, for controlling the neuropathic pain induced by lesion or alteration of the nervous system, both central and peripheral. Lastly, recent evidence has revealed the capacity of PEA to reduce neuroinflammation, which characterizes numerous diseases of the central nervous system, such as Multiple sclerosis and the Alzheimer's disease.

FAAH (Fatty Acid Amide Hydrolase) and NAAA (N-Acylethanolaminehydrolyzing Acid Amidase) enzymes are specific endogenous-hydrolases, which degrade, more or less specifically, N-Acylethanolamines (NAE); NAAA, in particular is currently considered a specific amidase for the degradation of the PEA. N-acylethanolamines degradation enzymes were considered, for a few years, therapeutic targets in that it was deemed that blocking them, more or less specifically, leading to the tissue increase of endogenous PEA, could be useful for curing inflammatory diseases also associated to pain. In particular, it was revealed that both the genetically FAAH-less animal phenotype (FAAH-knockout animals), and the pharmacological block of the enzyme, determine the reduction of the inflammatory response in numerous experimental models. With the aim of obtaining the pharmacological block of FAAH, various compounds having "URB-n"-marked carbamate chemical structure were synthesised, capable of irreversibly inhibiting FAAH. In particular a URB597-marked molecule (cyclohexyl carbamic acid 3'-carbamoyl-biphenyl-3-yl ester) revealed capable of considerably reducing the inflammation in various experimental models, including carrageenan edema, experimental colitis, inflammatory response of LPS-induced hypothalamus and LPS inflammatory pain. Intraperitoneal administration of such compounds have considerable adverse effects on the Central Nervous System. Recent studies have lead to the synthesis of enzymatic blockers of FAAH, of the so-called second generation type, still of the carbamate chemical type, including the URB694-marked compound, characterized both by greater reactivity with respect to FAAH, and by more favourable pharmacokinetic characteristics. Lastly molecules capable of blocking peripheral FAAH without affecting the central system were synthesised. Such studies have led to the synthesis of a p-hydroxyphenyl, derivative marked URB937, not capable of traversing the integral haemato-encephalic barrier.

Other studies instead concentrated on a series of FAAH blockers belonging to the family of aryl piperazinyl ureas, including a compound marked JNJ-1661010: a molecule that revealed to be selective in the inhibition of FAAH-2, through a semi-stable covalent bond with the same enzyme.

Other research groups synthesized blockers of specific enzymes, having the imide function inserted in a beta-lactam ring, capable of reversibly inhibiting FAAH.

Besides the FAAH blockers, selective NAAA enzyme blockers, which NAAA being considered highly specific for the degradation of PEA, were also recently synthesised such as, for example, (S)—N-(2-oxo-3-oxetanyl)-3-phenylpropionamide, capable of selectively blocking NAAA and, hence, the degradation of PEA.

In the research of molecules more or less selective but more and more active at blocking FAAH and/or NAAA with the aim of determining the increase of the endogenous levels of N-acylethanolamines, and in particular PEA, it has not been considered up to date that the pharmacological block obtained with non-physiologic substances and thus not rapidly metabolisable physiologically, may determine metabolic alterations—even quite considerable—for the organism. And this being due to the fact that the regulatory role of enzymes intended to modulate the availability of substrates, such as PEA, produced on demand by specific cells of the organism (such as for example mastocites, microglia, astroglia, in turn intended to regulate the central or peripheral sensitisation) is extremely difficult. It was actually observed that blocking FAAH is capable of determining cellular inflammatory hyperactive paradoxical effects. This probably depends on the fact that, in order to suitably exert the regulatory effect thereof on cells implicated in the neurogenic inflammation and neuroinflammation activity, PEA—upon the determination of the pleiotropic effect on the receptor complex (PPAR-$\alpha$, CB2, GPR-55, etc) involved in the activation of the regulation cells—must be quickly transformed into the components thereof (palmitic acid and ethanolamine). Furthermore, a paradoxical effect ensuing the blocking of FAAH (for example by URB597) was repeatedly documented; the blocking of the degradation enzymes determines an unbalancing of the endocannabinoid system consisting, for example, in a reduction of the levels of 2-Arachidonoylglycerol (2-AG) in given cerebral areas and in the spinal cord simultaneously with the increase of Anandamide (AEA), an increase that revealed to be actually quite dangerous due to the alterations of the tonic effect on the CB receptors and in particular on $CB_1$.

It should also be borne in mind that many of the synthetic blockers of the degradation enzymes of the N-acylamides, known up to date, reveal poor selectivity against target enzymes. URB597, for example, inhibits hepatic esterases by more than 40%.

From what has been mentioned above there arises the need, in presence of potentially inflammatory stimuli, for pharmacologically modulating—and not blocking—the specific amidases for N-acylamides and in particular the NAAA enzyme, so as not to alter the sensitive regulation biologic balance of the cells which, in order to maintain the correct homeostasis thereof, use the biological mechanisms complex, closely interconnected to each other, of rapid on demand synthesis and equally rapid degradation of PEA.

Among the oxazole and thiazole chemical structures known up to date, the only ones used for trying to inhibit FAAH include some ketoheterocyclic structures (in practice keto-oxazoles or keto-thiazoles).

On the contrary, though known from the literature oxazoline derivatives of fatty acids, this type of structures have never been evaluated up to date for the inhibition of FAAH and/or NAAA, or for possible inhibition activity on the inflammatory processes.

In particular PEA oxazoline has been used—up to date—exclusively as a synthesis intermediate in the preparation of special poly-2-oxazoline polymers.

SUMMARY OF THE INVENTION

The inventors of the present patent application surprisingly discovered that the modulation of NAAA, a specific degradation enzyme of PEA, can be obtained, pharmacologically, by a new method consisting in using oxazole or thiazole molecules, simultaneously having with two important activities: a) the capacity of modulating—and not blocking—the enzymatic activity of the specific amidase of PEA (the NAAA enzyme mentioned above); b) the capacity of being rapidly transformed, through entirely physiological processes, into PEA, a specific substrate for the same enzyme.

Thus, a molecule simultaneously provided with both the aforementioned activities is capable, on one hand, of optimizing the NAAA enzymatic activity, thus determining the maximum availability of biologically useable acylamide (in particular PEA) and, simultaneously, guaranteeing—through the activity of the specific amidase—the indispensable "return" to the biological system, of the components of the acylamide molecule (palmitic acid and ethanolamine in the case of PEA), thus avoiding interfering with the further on-demand physiological synthesis of PEA.

In particular the inventors of the present patent application "surprisingly discovered" that the oxazoline of PEA is capable of simultaneously efficiently inhibiting—though weakly with respect to the blockers known up to date—the NAAA enzyme contrary to the analogous non-cyclic structure (PEA) and, thus, determining an anti-inflammatory effect markedly greater than that determined by the analogous non-cyclic structure (PEA).

Furthermore, the inventors discovered that other oxazole, oxazine or thiazole structures derived from acylamides of saturated or monounsaturated fatty acids with chain comprised between 14 and 20 carbons, some of which are known and others unknown, are also capable of determining the inhibition of the NAAA enzyme.

DETAILED DESCRIPTION OF THE INVENTION

The present invention refers to a compound of general formula (I):

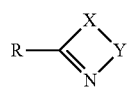

(I)

enantiomers, diastereoisomers, racemes and mixtures, polymorphs, salts, solvates thereof wherein:

(a) R is a linear alkyl radical having 13 to 19 carbon atoms or alkenyl radical having 13 to 19 carbon atoms carrying a double bond;
(b) X is O or S;
(c) Y is a 2 or 3 carbon atom alkylene residue, optionally substituted with one or two groups equal or different from each other and selected from among the group consisting of: —CH₃, —CH₂OH, —COOCH₃, —COOH.

Y may preferably be: —CH₂—CH₂—, —CH₂—CH₂—CH₂—, —CH(CH₃)—CH₂—, —CH₂—CH(CH₃)—, —CH₂—C(CH₃)₂—, —CH₂—CH(CH₂OH)—, —CH₂—C((CH₂OH)₂)—, —CH═CH—, —CH₂—CH(COOCH₃)—, —CH₂—CH(COOH)—, for use as a medicine.

In particular, the invention regards a compound of formula (I), as defined above, for use as a modulator of the NAAA enzyme.

According to a preferred aspect, the invention regards a compound of formula (I) as defined above for use as an anti-inflammatory.

According to a preferred aspect, the compounds of formula (I) have X=oxygen.

A further object of the invention are the compounds of general formula (I) as defined above, provided that, when X is oxygen, R is not a C13, C15 or C17 saturated or unsaturated radical.

Preparation of the Compounds of the Invention

The preparation of heterocyclic compounds referable to the general formula (I) of the present invention (2-oxazolines, 2-oxazines, 2-thiazolines, 2-oxazoles) are widely documented in scientific and patent literature (Vorbuggen H. Tetrahedron 1993, vol. 49, 9353-9372 and references included). The compounds of the invention were prepared according to the described methods, introducing suitable adaptations from time to time useful for improving the methods in terms of the inexpensiveness and safety of the process, quality and yield of the products. They were generally obtained through condensation reactions from corresponding amides of carboxylic acids of formula (Ia).

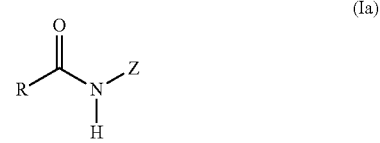

(Ia)

wherein Z is a group Y—X—H or a group —CH₂—CH(OR'OR"), R, Y and X have the meaning indicated for formula (I) and R' and R" may be —CH₃, —C₂H₅ or together constitute a propylene residue to form with the two oxygen atoms and the adjacent carbon a dioxolane residue.

The compounds of formula (Ia) were subjected to condensation-cyclization reaction to obtain the heterocyclic compounds of formula (I) subject of the invention. The condensation-cyclization reactions were carried out starting from the compounds of formula (Ia) in presence of suitable condensing agents or catalysts, at ambient temperature or by heating at a temperature comprised between 150 and 350° C. or using microwaves.

The synthesis of the compounds of the invention was further described through the following preparation examples, added solely by way of non-limiting example of the invention.

The preparation examples 1-6 refer to products known in literature, but described for uses different from those claimed by the present invention.

Example 1

Preparation of 2-pentadecyl-2-oxazoline (PEA-OXA)

3.0 g of N-(2-hydroxyethyl)palmitamide are suspended at 0° C. and under nitrogen gas atmosphere in 20 ml of $SOCl_2$. The mixture is stirred at 0° C. for 30 minutes, then at ambient temperature for 15 hours. The solution thus obtained is dry evaporated at a low pressure. The residue is purified by crystallization from 15 ml of tert-butyl methyl ether, isolated and dried under vacuum. The crystallized product is suspended in 20 ml of anhydrous toluene and 1.3 g of potassium tert-butoxide are added. The mixture is heated at 40° C. for 2 hours, then it is cooled at 4° C. The solution is extracted 3 times using 6 ml of water and the extracts are disposed. The organic phase is dry evaporated at a low pressure and the residue is distilled under high vacuum at about 0.5 mm Hg. The fraction which distillates at about 175° C. and solidifies at ambient temperature is collected and preserved in inert atmosphere. (About 92% yield)

The 2-pentadecyl-2-oxazoline product has the following characteristics: Molecular formula $C_{18}H_{35}NO$; C=76.81%, H=12.53%, N=4.94%, O=5.68%; Mr 281.5; ESI-MS: 282 (MH+); Melting point 46-48° C.; Solubility: poorly soluble in water, >10 mg/ml in ethanol.

Example 2

Preparation of 2-heptadecyl-2-oxazoline (SEA-OXA)

3.28 g of N-(2-hydroxyethyl)octadecanamide are suspended at 0° C. and under nitrogen gas atmosphere in 20 ml of $SOCl_2$. The mixture is stirred at 0° C. for 30 minutes, then at ambient temperature for 15 hours. The solution thus obtained is dry evaporated at a low pressure. The residue is purified by crystallization from 15 ml of ethyl acetate, isolated and dried under vacuum. The crystallized product is suspended in 20 ml of anhydrous toluene and 1.3 g of potassium tert-butoxide are added. The mixture is heated at 40° C. for 2 hours, then it is cooled at 4° C. The solution is extracted 3 times using 6 ml of water and the extracts are disposed. The organic phase is dry evaporated at a low pressure and the residue is distilled under high vacuum at about 0.01 mm Hg. The fraction which distillates at about 225° C. and solidifies at ambient temperature is collected and preserved in inert atmosphere. (About 90% yield)

The 2-heptadecyl-2-oxazoline product has the following characteristics: Molecular formula $C_{20}H_{39}NO$; C=77.61%, H=12.70%, N=4.53%, O=5.68%; Mr 309.5; ESI-MS: 310 (MH+); Melting point 51-53° C.; Solubility: poorly soluble in water, >10 mg/ml in ethanol.

Example 3

Preparation of 2-tridecyl-2-oxazoline (MEA-OXA)

2.72 g of N-(2-hydroxyethyl)myristamide are suspended at 0° C. and under nitrogen gas atmosphere in 20 ml of $SOCl_2$. The mixture is stirred at 0° C. for 30 minutes, then at ambient temperature for 15 hours. The solution thus obtained is dry evaporated at a low pressure. The residue is purified by crystallization from 15 ml of tert-butyl methyl ether, isolated and dried under vacuum. The crystallized product is suspended in 20 ml of anhydrous toluene and 2.6 g of silver trifluoromethanesulfonate are added. The mixture is heated at 40° C. for 2 hours, then it is cooled at 4° C. The formed whitish precipitate is separated by filtration, the solution is extracted 3 times using 6 ml of water and the extracts are disposed. The organic phase is dry evaporated at a low pressure and the residue is distilled under high vacuum at about 0.5 mm Hg. The fraction which distillates at about 160° C. and solidifies at ambient temperature is collected and preserved in inert atmosphere. (About 90% yield)

The 2-tridecyl-2-oxazoline product has the following characteristics: Waxy solid; Molecular formula $C_{16}H_{31}NO$; C=75.83%, H=12.33%, N=5.53%, O=6.31%; Mr 253.5; ESI-MS: 254 (MH+); Solubility: poorly soluble in water, >10 mg/ml in ethanol.

Example 4

Preparation of 2-(8-heptadecenyl)-2-oxazoline (OEA-OXA)

3.26 g of N-(2-hydroxyethyl)oleamide are suspended at 0° C. and under nitrogen gas atmosphere in 20 ml of $SOCl_2$. The mixture is stirred at 0° C. for 30 minutes, then at ambient temperature for 5 hours. The solution thus obtained is dry evaporated at a low pressure. The residue is used without further purification. It is suspended in 20 ml of anhydrous toluene and 1.3 g of potassium tert-butoxide are added. The mixture is heated at 40° C. for 2 hours, then it is cooled at 4° C. The solution is extracted 3 times using 6 ml of water and the extracts are disposed. The organic phase is dry evaporated at a low pressure and the brownish residue is purified by distillation under high vacuum at about 0.5 mm Hg. The fraction which distillates at about 180° C. is collected and preserved in inert atmosphere. (Yield: about 88%)

The 2-(8-heptadecenyl)-oxazoline product has the following characteristics: Molecular formula C20H37NO; C=78.12%, H=12.13%, N=4.55%, O=5.20%; Solubility: poorly soluble in water, >10 mg/ml in ethanol; Mr 307.5; ESI-MS: 308 (MH+).

Example 5

Preparation of 2-pentadecyl-4,4-dimethyl-2-oxazoline 2.7 g of methyl palmitate are mixed with 5 g of 2-amino-2-methyl-1-propandiol and heated at reflux in a flask equipped with condenser at 120° C. for 5 hrs in nitrogen atmosphere. The methanol produced by reaction and the excess 2-amino-2-methyl-1-propandiol are eliminated by distillation under vacuum. The raw amide thus obtained is used without further purification. The residue is heated once again at 200° C. for 6 hrs under vacuum of 15 mm Hg to eliminate the water produced by the condensation. The obtained residue is purified by distillation under high vacuum at 0.05 mm Hg. (Yield: about 90%)

The 2-pentadecyl-4,4-dimethyl-2-oxazoline product has the following characteristics: Molecular formula C20H39NO; C=77.61%, H=12.70%, N=4.53%, O=5.17%; Solubility: poorly soluble in water, >10 mg/ml in ethanol; Mr 309.5; ESI-MS: 310 (MH+).

Example 6

Preparation of 2-pentadecyl-4,4-bis(hydroxymethyl)-2-oxazoline 2.7 g of methyl palmitate are mixed with 5 g of 2-amino-2-hydroxymethyl-1,3-propandiol and heated at reflux in a flask equipped with condenser at 120° C. for 5 hrs in nitrogen atmosphere. The mixture is cooled and the residue solubilised using 40 ml of ethyl acetate. The solution is extracted 3 times using 10 ml of water, which is disposed. The organic phase is dry evaporated under vacuum. The raw amide thus obtained is used without further purification. The residue is heated once again at 200° C. for 6 hrs under vacuum of 15 mmHg to eliminate the water produced by the condensation. The obtained residue is purified by cold crystallization from ethyl acetate. (Yield: about 90%)

The 2-pentadecyl-4,4-bis(hydroxymethyl)-2-oxazoline product has the following characteristics: Molecular formula $C_{20}H_{39}NO_3$; C=70.34%, H=11.51%, N=4.10%, O=14.05%; Solubility: poorly soluble in water, >10 mg/ml in ethanol; Mr 341.5; ESI-MS: 342 (MH+).

Example 7

Preparation of 2-tetradecyl-2-oxazoline (C15EA-OXA)

2.56 g of methyl pentadecanoate are mixed with 5 g ethanolamine and heated at reflux in a flask equipped with condenser at 120° C. for 5 hrs under nitrogen atmosphere. The methanol produced by reaction and the excess ethanolamine are eliminated by distillation under vacuum. The residue is solubilised using 50 ml of ethyl acetate. The solution is extracted 3 times using 10 ml of water, which is disposed. The organic phase is anhydrified using $Na_2SO_4$ and dry evaporated under vacuum. The raw amide thus obtained is used without further purification. The residue is suspended at 0° C. and under nitrogen gas atmosphere in 20 ml of $SOCl_2$. The mixture is stirred at 0° C. for 30 minutes, then at ambient temperature for 15 hours. The solution thus obtained is dry evaporated at a low pressure. The residue is purified by crystallization from 15 ml of tert-butyl methyl ether, isolated and dried under vacuum. The crystallized product is suspended in 20 ml of anhydrous toluene and 1.3 g of potassium tert-butoxide are added. The mixture is heated at 40° C. for 2 hours, then it is cooled at 4° C. The solution is extracted 3 times using 6 ml of water and the extracts are disposed. The organic phase is dry evaporated at a low pressure and the residue is distilled under high vacuum at about 0.5 mmHg. The fraction which distillates at about 165° C. and solidifies at ambient temperature is collected and preserved in inert atmosphere. (About 94% yield)

The 2-tetradecyl-2-oxazoline product has the following characteristics: Molecular formula $C_{17}H_{33}NO$; C=76.34%, H=12.44%, N=5.24%, O=5.98%; Solubility: poorly soluble in water, >10 mg/ml in ethanol; Mr 267.5; ESI-MS: 268 (MH+); Melting point 41-44° C.

Example 8

Preparation of 2-hexadecyl-2-oxazoline (C17EA-OXA)

2.85 g of methylheptadecanoate are mixed with 5 g of ethanolamine and heated at reflux in a flask equipped with condenser at 120° C. for 5 hrs under nitrogen atmosphere. The methanol produced by reaction and the excess ethanolamine are eliminated by distillation under vacuum. The residue is solubilised using 50 ml of ethyl acetate. The solution is extracted 3 times using 10 ml of water, which is disposed. The organic phase is anhydrified using $Na_2SO_4$ and dry evaporated under vacuum. The raw amide thus obtained is used without further purification. The residue is suspended at 0° C. and under nitrogen gas atmosphere in 20 ml of $SOCl_2$. The mixture is stirred at 0° C. for 30 minutes, then at ambient temperature for 15 hours. The solution thus obtained is dry evaporated at a low pressure. The residue is purified by crystallization from 15 ml of ethyl acetate, isolated and dried under vacuum. The crystallized product is suspended in 20 ml of anhydrous toluene and 1.3 g of potassium tert-butoxide are added. The mixture is heated at 40° C. for 2 hours, then it is cooled at ambient temperature. The solution is extracted 3 times using 6 ml of water and the extracts are disposed. The organic phase is dry evaporated at a low pressure and the residue is distilled under high vacuum at about 0.5 mmHg. The fraction which distillates at about 190° C. and solidifies at ambient temperature is collected and preserved in inert atmosphere. (About 90% yield)

The 2-hexadecyl-2-oxazoline product has the following characteristics: Molecular formula $C_{19}H_{37}NO$; C=77.23%, H=12.62%, N=4.74%, O=5.41%; Solubility: poorly soluble in water, >10 mg/ml in ethanol; Mr 295.5; ESI-MS: 296 (MH+); Melting point 49-51° C.

Example 9

Preparation of 2-pentadecyl-5(R)-methyl-2-oxazoline 2.7 g of methyl palmitate are mixed with 5 g of R-(-)-1-amino-2-propanol and heated at reflux in a flask equipped with condenser at 120° C. for 5 hrs under nitrogen atmosphere. The methanol produced by reaction and the excess amine are eliminated by distillation under vacuum. The residue is solubilised using 50 ml of ethyl acetate. The solution is extracted 3 times using 10 ml of water, which is disposed. The organic phase is anhydrified using $Na_2SO_4$ and dry evaporated under vacuum. The raw amide thus obtained is used without further purification. The residue is suspended at 0° C. and under nitrogen gas atmosphere in 20 ml of $SOCl_2$. The mixture is stirred at 0° C. for 30 minutes, then at ambient temperature for 15 hours. The solution thus obtained is dry evaporated at a low pressure. The residue is purified by crystallization from 15 ml of tert-butyl methyl ether, isolated and dried under vacuum. The crystallized product is suspended in 20 ml of anhydrous toluene and 1.3 g of potassium tert-butoxide are added. The mixture is heated at 40° C. for 2 hours, then it is cooled at 4° C. The solution is extracted 3 times using 6 ml of water and the extracts are disposed. The organic phase is dry evaporated at a low pressure and the residue is distilled under high vacuum at about 0.3 mmHg. The fraction which distillates at about 190° C. and solidifies at ambient temperature is collected and preserved in inert atmosphere. (About 90% yield)

The 2-pentadecyl-5(R)-methyl-2-oxazoline product has the following characteristics: Molecular formula $C_{19}H_{37}NO$; C=77.23%, H=12.62%, N=4.74%, O=5.41%; Solubility: poorly soluble in water, >10 mg/ml in ethanol; Mr 295.5; ESI-MS: 296 (MH+).

Example 10

Preparation of 2-pentadecyl-5(S)-methyl-2-oxazoline 2.7 g of methyl palmitate are mixed with 5 g of S-(+)-1-amino-2-propanol and heated at reflux in a flask equipped with condenser at 120° C. for 5 hrs under nitrogen atmosphere. The methanol produced by reaction and the excess amine are eliminated by distillation under vacuum. The residue is solubilised using 50 ml of ethyl acetate. The solution is extracted 3 times using 10 ml of water, which is disposed. The organic phase is anhydrified using $Na_2SO_4$ and dry evaporated under vacuum. The raw amide thus obtained is used without further purification. The residue is suspended at 0° C. and under nitrogen gas atmosphere in 20 ml of $SOCl_2$. The mixture is stirred at 0° C. for 30 minutes, then at ambient temperature for 15 hours. The solution thus obtained is dry evaporated at a low pressure. The residue is purified by crystallization from 15 ml of tert-butyl methyl ether, isolated and dried under vacuum. The crystallized product is suspended in 20 ml of anhydrous toluene, and 1.3 g of potassium tert-butoxide are added. The mixture is heated at 40° C. for 2 hours, then it is cooled at 4° C. The solution is extracted 3 times using 6 ml of water and the extracts are disposed. The organic phase is dry evaporated at a low pressure and the residue is distilled under high vacuum at about 0.3 mmHg. The fraction which distillates at about 190° C. and solidifies at ambient temperature is collected and preserved in inert atmosphere. (About 91% yield).

The 2-pentadecyl-5(S)-methyl-2-oxazoline product has the following characteristics: Molecular formula $C_{19}H_{37}NO$; C=77.23%, H=12.62%, N=4.74%, O=5.41%; Solubility: poorly soluble in water, >10 mg/ml in ethanol; Mr 295.5; ESI-MS: 296 (MH+).

Example 11

Preparation of
2-pentadecyl-4(R)-methyl-2-oxazoline 2.7 g of methyl palmitate are mixed with 5 g of R-(−)-2-amino-1-propanol and heated at reflux in a flask equipped with condenser at 120° C. for 5 hrs under nitrogen atmosphere. The methanol produced by reaction and the excess amine are eliminated by distillation under vacuum. The residue is solubilised using 50 ml of ethyl acetate. The solution is extracted 3 times using 10 ml of water, which is disposed. The organic phase is anhydrified using $Na_2SO_4$ and dry evaporated under vacuum. The raw amide thus obtained is used without further purification. The residue is suspended at 0° C. and under nitrogen gas atmosphere in 20 ml of $SOCl_2$. The mixture is stirred at 0° C. for 30 minutes, then at ambient temperature for 15 hours. The solution thus obtained is dry evaporated at a low pressure. The residue is purified by crystallization from 15 ml of tert-butyl methyl ether, isolated and dried under vacuum. The crystallized product is suspended in 20 ml of anhydrous toluene and 1.3 g of potassium tert-butoxide are added. The mixture is heated at 40° C. for 2 hours, then it is cooled at 4° C. The solution is extracted 3 times using 6 ml of water and the extracts are disposed. The organic phase is dry evaporated at a low pressure and the residue is distilled under high vacuum at about 0.3 mmHg. The fraction which distillates at about 190° C. and solidifies at ambient temperature is collected and preserved in inert atmosphere. (About 94% yield)

The 2-pentadecyl-4(R)-methyl-2-oxazoline product has the following characteristics: Molecular formula $C_{19}H_{37}NO$; C=77.23%, H=12.62%, N=4.74%, O=5.41%; Solubility: poorly soluble in water, >10 mg/ml in ethanol; Mr 295.5; ESI-MS: 296 (MH+).

Example 12

Preparation of
2-pentadecyl-4(S)-methyl-2-oxazoline 2.7 g of methyl palmitate are mixed with 5 g of S-(+)-2-amino-1-propanol and heated at reflux in a flask equipped with condenser at 120° C. for 5 hrs under nitrogen atmosphere. The methanol produced by reaction and the excess amine are eliminated by distillation under vacuum. The residue is solubilised using 50 ml of ethyl acetate. The solution is extracted 3 times using 10 ml of water, which is disposed. The organic phase is anhydrified using $Na_2SO_4$ and dry evaporated under vacuum. The raw amide thus obtained is used without further purification. The residue is suspended at 0° C. and under nitrogen gas atmosphere in 20 ml of $SOCl_2$. The mixture is stirred at 0° C. for 30 minutes, then at ambient temperature for 15 hours. The solution thus obtained is dry evaporated at a low pressure. The residue is purified by crystallization from 15 ml of tert-butyl methyl ether, isolated and dried under vacuum. The crystallized product is suspended in 20 ml of anhydrous toluene and 1.3 g of potassium tert-butoxide are added. The mixture is heated at 40° C. for 2 hours, then it is cooled at 4° C. The solution is extracted 3 times using 6 ml of water and the extracts are disposed. The organic phase is dry evaporated at a low pressure and the residue is distilled under high vacuum at about 0.3 mmHg. The fraction which distillates at about 190° C. and solidifies at ambient temperature is collected and preserved in inert atmosphere. (About 92% yield)

The 2-pentadecyl-4(S)-methyl-2-oxazoline product has the following characteristics: Molecular formula $C_{19}H_{37}NO$; C=77.23%, H=12.62%, N=4.74%, O=5.41%; Solubility: poorly soluble in water, >10 mg/ml in ethanol; Mr 295.5; ESI-MS: 296 (MH+).

Example 13

Preparation of
2-pentadecyl-4-hydroxymethyl-2-oxazoline

Method of Preparation:
0.91 g of 2-amino-1,3-propandiol and 1.13 g of triethylamine are solubilised in 15 ml of tetrahydrofuran at 0° C. The solution is stirred and placed under nitrogen atmosphere. A solution of 2.74 g of palmitoyl chloride is added dropwise slowly within 30 min. After another 30 min of stirring at ambient temperature, the mixture is dry evaporated. The residue is solubilised using 15 ml of ethyl acetate and extracted using 10 ml of water which is disposed. The organic phase is anhydrified using $Na_2SO_4$ and dry evaporated under vacuum. The raw amide thus obtained is used without further purification. The residue is suspended at 0° C. and under nitrogen gas atmosphere in 20 ml of $SOCl_2$. The mixture is stirred at 0° C. for 30 minutes, then at ambient temperature for 6 hours. The solution thus obtained is dry evaporated at a low pressure. The residue is purified by crystallization from 15 ml of tert-butyl methyl ether, isolated and dried under vacuum. The crystallized product is suspended in 20 ml of anhydrous toluene and 1.3 g of potassium tert-butoxide are added. The mixture is heated at 40° C. for 2 hours, then it is cooled at 4° C. The solution is extracted 3 times using 6 ml of water and the extracts are disposed. The organic phase is dry evaporated at low pressure and the residue purified through flash chromatography in a column of silica gel using—as eluent—a mixture of hexane and ethyl acetate 1:3. The fractions containing the pure product are recombined and dry evaporated under vacuum. (About 90% yield)

The 2-pentadecyl-4-hydroxymethyl-2-oxazoline product has the following characteristics: Molecular formula $C_{19}H_{37}NO_2$; C=73.26%, H=11.97%, N=4.50%, O=10.27%; Solubility: poorly soluble in water, >10 mg/ml in ethanol; Mr 311.5; ESI-MS: 312 ($MH_+$).

Example 14

Preparation of 2-pentadecyl-4-methyloxycarbonyl-2-oxazoline 7.78 g of L-serine methyl ester hydrochloride are solubilised in 200 ml of distilled water. The solution is cooled at 0° C. and 6.18 g of $K_2CO_3$ are added. A solution of 13.7 g of palmitoyl chloride in 50 ml of tetrahydrofuran are added dropwise slowly within 30 min to the solution of the methyl ester serine, under vigorous stirring. After another 30 min of stirring at 0° C., the aqueous phase is separated and extracted once again using 25 ml of tetrahydrofuran. The two organic phases are washed using 50 ml of saturated NaCl solution, then recombined and dry evaporated. The residue is purified by crystallization from 200 ml of tert-butyl methyl ether. 14.5 grams of pure N-palmitoyl-L-serine methyl ester intermediate are recovered.

The dry crystallized product is suspended at 0° C. and under nitrogen gas atmosphere in 100 ml of $SOCl_2$. The mixture is stirred at 0° C. for 30 minutes, then at ambient temperature for 6 hours. The solution thus obtained is dry evaporated at a low pressure. The residue is suspended in 200 ml of anhydrous toluene and 5.5 g of potassium tert-butoxide are added. The mixture is heated at 40° C. for 2 hours, then it is cooled at 4° C. The solution is extracted 3 times using 6 ml of water and the extracts are disposed. The organic phase is dry evaporated at a low pressure and the residue purified through flash chromatography in a column of silica gel using—as eluent—a mixture of hexane and ethyl acetate 1:5. The fractions containing the pure product are recombined and dry evaporated under vacuum. (about 88% yield).

The 2-pentadecyl-4-methyloxycarbonyl-2-oxazoline product has the following characteristics: Molecular formula $C_{20}H_{37}NO_3$; C=70.75%, H=10.98%, N=4.13%, O=14.14%; Solubility: poorly soluble in water, >10 mg/ml in ethanol; Mr 339.5; ESI-MS: 340 (MH+).

Example 14b

Preparation of 2-pentadecyl-4-carboxy-2-oxazoline 3.4 g of the product of example 14 are suspended in 100 ml of methanol/water 1:1 and treated using 10 ml of NaOH 1N. The mixture is heated at 45° C. for 1 hour under stirring, then the methanol is evaporated under vacuum. 11 ml of HCl 1N are added and the precipitated product is separated by filtration, washed 3 times using 10 ml of water and lastly dried under high vacuum. The amorphous solid is crystallized from 30 ml of ethyl acetate, separated by filtration and dried under high vacuum.

The 2-pentadecyl-4-carboxy-2-oxazoline product has the following characteristics: Molecular formula $C_{19}H_{35}NO_3$; C=70.11%, H=10.84%, N=4.30%, O=14.75%; Solubility: poorly soluble in water, >10 mg/ml in ethanol; Mr 325.5.

Example 15

Preparation of 2-pentadecyl-2-oxazine 3.14 of N-(3-hydroxypropyl)palmitamide are suspended at 0° C. and under nitrogen gas atmosphere in 20 ml of $SOCl_2$. The mixture is stirred at 0° C. for 30 minutes, then at ambient temperature for 8 hours. The solution thus obtained is dry evaporated at a low pressure. The residue is purified by crystallization from 15 ml of ethyl acetate, isolated and dried under vacuum. The crystallized product is suspended in 20 ml of anhydrous toluene and 1.3 g of potassium tert-butoxide are added. The mixture is heated at 45° C. for 3 hours, then it is cooled at 4° C. The solution is extracted 3 times using 6 ml of water and the extracts are disposed. The organic phase is dry evaporated at a low pressure and the residue is distilled under high vacuum at about 0.5 mmHg. The fraction which distillates at about 205° C. and solidifies at ambient temperature is collected and preserved in inert atmosphere. (About 88% yield)

The 2-pentadecyl-2-oxazine product has the following characteristics: Molecular formula $C_{19}H_{37}NO$; C=77.23%, H=12.62%, N=4.74%, O=5.41%; Solubility: poorly soluble in water, >10 mg/ml in ethanol; Mr 295.5. ESI-MS: 296 (MH+).

Example 16

Preparation of 2-pentadecyl-2-thiazoline 4.5 g of cystamine dihydrochloride and 2.26 g of triethylamine are solubilised in 15 ml of tetrahydrofuran at 0° C. The solution is stirred under nitrogen atmosphere. A solution of 2.74 g of palmitoyl chloride is added dropwise slowly within 30 min. After another 30 min of stirring at ambient temperature, the mixture is dry evaporated. The residue is solubilised using 15 ml of ethyl acetate and extracted using 10 ml of water which is disposed. The organic phase is dry evaporated under vacuum. The residue is recovered using 40 ml of methanol/water 3:1. The mixture is reduced with 200 mg of metal zinc in granules and 10 ml of hydrochloric acid 4N. After separation of the excess of metal zinc and concentration under vacuum at about 10 ml, the mass is extracted using 20 ml of ethyl acetate. The organic phase is washed 2 times using 10 ml of water, anhydrified using $Na_2SO_4$ and dry evaporated under vacuum. The raw thioamide thus obtained is used without further purification. The residue is suspended at 0° C. and under nitrogen gas atmosphere in 20 ml of Pyridine and 1.15 g of mesyl chloride are added. The reaction is maintained at 0° C. for 1 hour then brought to 45° C. and maintained under stirring for another 4 hours under nitrogen atmosphere. The solution is then dry evaporated at a low pressure. The residue is recovered using 30 ml of ethyl acetate and the solution is extracted 3 times using 10 ml of water which is disposed. The organic phase is evaporated under vacuum and the residue purified by crystallization from 15 ml of tert-butyl methyl ether. (About 84% yield on palmitoyl chloride)

The 2-pentadecyl-2-thiazoline product has the following characteristics: Molecular formula $C_{18}H_{35}NS$; C=72.66%, H=11.86%, N=4.71%, S=10.78%; Solubility: poorly soluble in water, >10 mg/ml in ethanol; Mr 297.5. ESI-MS: 298 (MH+).

Example 17

Preparation of 2-pentadecyl-2-oxazole 2.7 g of methyl palmitate are mixed with 1.05 g of aminoacetaldehyde dimethyl acetale and heated at reflux in a flask equipped with condenser at 110° C. for 3 hrs under nitrogen atmosphere. The methanol produced by reaction is eliminated by distillation under vacuum. The raw amide thus obtained is used without further purification. The residue is cooled at ambient temperature and 38.5 g of polyphosphoric acid are added, still under nitrogen atmosphere for removing humidity. The mixture is heated under stirring for 4 h at 150° C., then cooled and 100 g of water/ice mixture are added, lastly the mixture is neutralised with NaOH. The mixture is extracted 2 times using 20 ml of ethyl acetate. The organic phase is concentrated by evaporation under vacuum. The obtained brownish residue is purified by distillation under high vacuum at 0.05 mm Hg. (Yield: about 88%)

The 2-pentadecyl-2-oxazole product has the following characteristics: Molecular formula $C_{18}H_{33}NO$; C=77.36%, H=11.90%, N=5.01%, O=5.72%; Solubility: poorly soluble in water, >10 mg/ml in ethanol; Mr 279.5; ESI-MS: 279 (MH+); Melting point: deliquescent solid.

BIOLOGICAL EXAMPLES a) Method for Determining the Activity on the NAAA Enzyme

The effect of the samples being analysed on the enzymatic activity of the NAAA (N-Acylethanolamine Hydrolizing Acid Amidase) was determined on suitably permanently transfected cellular lines (HEK-NAAA). The cells were homogenised using TRIS-HCl 20 Mm (pH 7.4) by means of dounce. Subsequently a mild centrifugation (10 min, 800 g, 4° C.) was carried out for removing the cellular debris. The cellular fraction containing the membranes was obtained by means of subsequent centrifugation (30 min, 12000 g, 4° C.). The membranes (50 µg/sample) were incubated for 30 min at 37° C. with [$^{14}$C]PEA (20 µM; 10000 cpm/sample; 5 nCi/nmols) in presence and in absence of the substances to be tested. The incubation was blocked by adding 2 volumes of $CHCl_3/CH_3OH$ (1:1/v:v). The radioactivity associated to the aqueous phase containing [$^{14}$C]Ethanolamine (produced by the hydrolysis of the radioactive substrate) was determined by means of β-Counter (Beckman Counter, LS6500 Scintillation Counters, Milan).

Obtained Results

Table 1 shows the mean data obtained from 10 experiments:

TAB 1

| Tested compounds | Inhibition of NAAA IC50 (after 30 min incubation) |
| --- | --- |
| PEA (Palmitoylethanolamide) | >50.0 µM |
| SEA (Stearylethanolamide) | >50.0 µM |
| OEA (Oleoylethanolamine) | >50.0 µM |
| MEA (Myristoyl ethanolamide) | >50.0 µM |

TAB 1-continued

| Tested compounds | Inhibition of NAAA IC50 (after 30 min incubation) |
| --- | --- |
| PEA-OXA (example 1 compound) | 24.2 ± 0.018 µM |
| SEA-OXA (example 2 compound) | 35.0 ± 0.021 µM |
| MEA-OXA (example 3 compound) | 41.5 ± 0.032 µM |
| OEA-OXA (example 4 compound) | 38.4 ± 0.034 µM |
| PEA-OXLE (example 17 compound) | 32.1 ± 0.031 µM |
| (S)-N-(2-oxo-3-oxetanyl)-3-phenylpropionamide (known example of NAAA exogenous synthetic blocker) | 0.42 µM |

As observable, the compounds of the invention cause the partial'inhibition of NAAA if compared with the (S)—N-(2-oxo-3-oxetanyl)-3-phenylpropionamide exogenous blocker, which suitably adapts to the object of obtaining a modulation of the activity of the enzyme on which the present invention is based. The state of the art compounds instead, i.e. PEA, SEA, OEA and MEA, all show not-determined IC50 in that greater than 50 µM, thus not revealing any inhibitory activity with respect to NAAA.

B) Method for Determining Anti-Inflammatory Activity

The experimental model of edema of the legs is induced through sub-plantar injection of a carrageenan solution (containing 50 µl of sterile saline solution and 1% of carrageenan) in the right leg of the animal (rat).

At specific time intervals the plantar volume is measured by means of a plethysmometer (Ugo Basile, Milan, Italy). The increase of the plantar volume is evaluated as the difference between the value obtained in the specific time intervals and the volume at the basal (time 0) measured immediately before the administration of carrageenan.

Obtained Results

The data obtained from 5 different experiments, each involving 10 animals per group, were tabled (tab 2) in percentage with respect to the animals treated with carrageenan alone (carrageenan=100):

TABLE 2

| | 30 min | 1 hr | 2 hrs | 3 hrs | 4 hrs | 5 hrs | 6 hrs |
| --- | --- | --- | --- | --- | --- | --- | --- |
| Carrageenan | 100.0 | 100.0 | 100.0 | 100.0 | 100.0 | 100.0 | 100.0 |
| Carrageenan + PEA (33 µM/Kg) | 89.2 ± 2.2 | 82 ± 1.8 | 78.3 ± 1.6 | 73.9 ± 2.1 | 70.1 ± 1.9 | 54.5 ± 0.63 | 32.9 ± 0.41 |
| carrageenan + PEA-OXA (example 1 compound) (30 mg/Kg) µM/Kg | 88.2 ± 2.0 | 81.2 ± 2.1 | 66.6 ± 0.78 | 59.6 ± 0.62 | 51.4 ± 0.58 | 43.0 ± 0.42 | 31.2 ± 0.22 |

The data indicated above show that the compound of the invention (PEA-OXA) has a greater anti-inflammatory activity with respect to that of the analogous PEA of the prior art, especially between 2 and 5 hours from the administration of carrageenan.

As described previously, without reference to a particular theory, it seems that the pharmacological effect is mediated by the capacity of the 2-oxazolines, 2-oxazines, 2-thiazolines and 2-oxazoles derived from N-acyl-alkanolamines—and in particular oxazoline of PEA—to modulate in an inhibitory manner the activity of the specific degradation enzymes—in particular of NAAA thus determining the maximum availability of biologically useable acylamide (in particular of PEA) and, at the same time, guaranteeing the indispensible "restitution" to the biological system, the components of the acylamide molecule (in the case of PEA, palmitic acid and ethanolamine), thus avoiding interfering with—as it instead occurs using exogenous synthetic substances that block said enzymes—the further on-demand physiological synthesis of PEA.

Thus, a compound of formula (I) as defined above for use as an inhibitory modulator of the activity of the FAAH and NAAA enzymes constitutes an object of the invention.

A further object of the invention is a compound of formula (I) for the use defined above in combination with one or more different compounds of formula (I) or with palmitoylethanolamide, for a combined, separate or sequential administration.

The compounds of formula (I) may be used as anti-inflammatory agents. In particular, the compounds of the invention may be used in the treatment of:

1—neuro-immunogenic inflammatory processes at the level of peripheral organs and systems of the organism which support diseases such as a) the irritable bowel syndrome, Crohn's disease, coeliac disease; b) interstitial cystitis, recurrent cystitis, inflammations associated to chemotherapy treatments used in the treatment of bowel carcinoma; c) vulvodynia, vestibulodynia, vulvar vestibulitis; d) vaginitis of different aetiology; e) endometriosis lesions; f) chronic nonbacterial prostatitis, benign prostatic hypertrophy; g) myasthenia gravis; h) arthropathies of traumatic or degenerative or immunological origin affecting the mobile and/or semimobile joints; i) the painful diseases of the intervertebral discs due to neo-innervation and neo-vascularisation of the cartilaginous tissue and of the attached ligamentous structures—pulposus nucleus (nucleus pulposus) and/or fibrous rings (anulus fibrosus), anterior and posterior longitudinal ligaments, supraspinous ligament; j) cephalgia syndromes due to and not due to the inflammation of the meningeal tissue; k) inflammations of the mucous and mucocutaneousus tissues of the oral cavity and of the dental pulp; l) inflammatory-based diseases of the skin and of the cutaneousus appendages such as skin and scalp seborrhoeic dermatitis, acne, pityriasis versicolor, contact dermatitis, irritative contact dermatitis, atopic dermatitis, psoriasis, lichen planus, lupus erythematosus, alopecia aereata m) inflammatory-based diseases of the venous system such as chronic venous insufficiency, coronary restenosis after angioplasty, atherosclerosis; n) inflammatory-based diseases of the respiratory system such as asthma, rhinitis, pharyngitis, laryngitis, bronchitis, tonsillitis, recurrent coughing; o) self-inflammatory-based recurrent fever of the PFAPA type in paediatric and non-paediatric age; p) neuropathic-based dermoepidermal neuralgia of the small fibres, nociceptive and/or pruriceptive, such as postherpetic neuralgia, neuralgia associated to diabetes, neuralgia due to HIV infection, neuropathic and/or psychogenic itch; q) granuloma affecting the dermoepidermic tissue; r) aderential syndromes due to peritonitis and/or laparotomic and/or laparoscopic surgical interventions; s) dermatological diseases, even of the immunological genesis type, characterised by neuroinflammatory processes, both acute and chronic; t) high inflammatory component diseases of the ocular region, both acute and chronic, such as uveitis, iritis, iridocyclitis, glaucoma, scleritis, conjunctivitis, keratoconjunctivitis, blepharitis, optic neuritis, retinitis pigmentosa, chorioretinitis, dry eye syndrome and in particular Sjogren's syndrome; u) the diseases of the auricular region with high inflammatory component such as external ceruminous otitis, external eczematous otitis, otitis media in acute recurrent or chronic form, catarrhal otitis media, otitis interna, Meniere's syndrome, vestibular neuronitis; v) diseases from altered osteosynthesis/osteolysis ratio; w) inflammatory, toxic, infective, traumatic, dysmetabolic-based painful and non-painful diseases of the peripheral nerve.

2—neuroinflammatory processes, also associated to neurodegeneration, which occur affecting nervous structures of the spinal cord due to: a) traumatic, dysmetabolic or degenerative noxae such as stenosis of the medullary cavity such as spondylisis and spondylolisthesis or traumatic lesions due to flexo-extension of the spine; b) inflammatory distresses affecting encephalic nervous structures (stroke, multiple sclerosis, Parkinson's disease, fibromyalgic syndrome) with ensuing occurrence of peripheral pains, currently classified as Central Pain Syndromes; c) chronic inflammatory distresses of the Osteoarticular System, of arthritic or arthrosis or traumatic origin, and of the Peripheral Nervous System mainly characterized by chronic and/or neuropathic pain;

3—neuroinflammatory processes, also associated to neurodegenaration, which occur affecting nervous structures of given encephalic areas due to traumatic, neuro-toxic, dysmetabolic, or degenerative noxae such as hypoxic distress states (stroke, TIA-Trans Ischemic Attack), senile and presenile dementias also of the Alzheimer type, cranio-encephalic traumas, Parkinson's disease, Multiple sclerosis, Amiotrophic Lateral Sclerosis.

The compounds of the invention may be formulated for oral, buccal, parenteral, rectal, intravesical or transdermal administration or in a form suitable for administration by inhalation or insufflation (both through the mouth and nose).

For the oral administration, the pharmaceutical compositions may, for example, be in form of tablets or capsules prepared conventionally using pharmaceutically acceptable excipients such as bonding agents (for example pregelatinised maize starch, polyvinylpyrrolidone or hydroxypropyl methylcellulose); filler agents (for example lactose, microcrystalline cellulose or calcium hydrogen phosphate); lubricants (for example magnesium stearate, talc or silica); disintegration agents (for example potato starch or sodium glycolate starch); or inhibiting agents (for example sodium lauryl sulfate). The tablets may be coated using the methods well known in the art. The liquid preparations for the oral administration may, for example, be in form of solutions, syrups or suspensions or they may be in form of lyophilized or granulated products to be reconstituted, before use, using water or other suitable carriers. Such liquid preparations may be prepared through conventional methods using pharmaceutically acceptable additives such as suspension agents (for example sorbitol syrups, cellulose or edible hydrogenated fats derivatives); emulsifying agents (for example lecithin or acacia); non-aqueous carriers (for example almond oil, oil-based esters, ethylic alcohol or fractionated vegetable oils); and preservatives (for example methyl- or propyl-p-hydroxybenzoates or sorbic acid). The preparation may also suitably contain flavours, colouring agents and sweetening agents.

The preparations for oral administration may be suitably formulated to allow the controlled release of the active ingredient.

For the buccal administration, the compositions may be in, form of tablets, pills or granules formulated conventionally, suitable for absorption at the buccal-mucosa level. Typical buccal formulations are tablets for sublingual administration.

The compounds according to the present invention may be formulated for a parenteral administration by injection. The formulations for the injections may be in form of a single dosage for example in phials, with preservative added. The compositions may be in such form as suspensions, solutions or emulsions in oil-based or aqueous carriers and they may contain formulary agents such as suspension, stabilisation and/or dispersion agents. Alternatively, the active ingredient may be in form of powder to be reconstituted, before use, using a suitable carrier, for example using sterile water.

According to the present invention, the compounds may also be formulated according to rectal compositions such as suppositories or retention enema, for example containing the basic components of the common suppositories such as cocoa butter or other glycerides.

For topical administration, the compounds of the invention may be formulated as creams, ointments, gels, eye-drops or other formulations commonly used for such purpose.

In addition to the previously described compositions, the compounds may also be formulated as depot preparations. Such long action formulations may be administered by implantation (for example through subcutaneous, transcutaneous or intramuscular implantation) or by intramuscular injection. Thus, for example, the compounds, according to the present invention may be formulated using suitable polymeric or hydrophobic materials (for example in form of an emulsion in a suitable oil) or ion-exchange resins or as minimally soluble derivatives, for example as a minimally soluble salt.

According to the present invention the dosage of the compounds proposed for administration to a man (with body weight of about 70 Kg) ranges between 0.1 mg and 1 g and, preferably between 1 mg and 600 mg of the active ingredient per dosage unit. The dosage unit may be administered, for example, 1 to 4 times per day. The dosage will depend on the selected method of administration. It should be considered that there may arise the need of continuously varying the dosage depending on the age and weight of the patient as well as the seriousness of the clinical condition to be treated. Lastly, the exact dosage and method of administration will be at the discretion of the medical doctor or veterinarian administering the dosage.

The pharmaceutical compositions of the invention may be prepared according to conventional methods, such as for example those described in Remington's Pharmaceutical Sciences Handbook, Mack Pub. Co., N.Y., USA, 17th edition, 1985.

EXAMPLES OF FORMULATIONS

Example A

Tablets for Oral Use

Each tablet contains:

| | |
|---|---|
| PEA-OXA | mg 300.00 |
| Microcrystalline cellulose | mg 78.47 |
| Croscarmellose sodium | mg 45.00 |
| Polyvinylpyrrolidone | mg 10.00 |
| Magnesium stearate | mg 4.00 |
| Polysorbate 80 | mg 2.00 |
| Gastro-resistant coating based on macrogol 400, copolymer of methacrylic acid-ethyl acrylate (1:1), polysorbate 80 | |

Example B

Tablets for Oral Use

Each tablet contains:

| | |
|---|---|
| PEA-OXA | mg 600.00 |
| Microcrystalline cellulose | mg 156.94 |
| Croscarmellose sodium | mg 90.00 |
| Polyvinylpyrrolidone | mg 20.00 |
| Magnesium stearate | mg 8.00 |
| Polysorbate 80 | mg 4.00 |
| Gastro-resistant coating based on macrogol 400, copolymer of the methacrylic acid-ethyl acrylate (1:1), polysorbate 80 | |

Example C

Tablets for Oral Use

Each tablet contains:

| | |
|---|---|
| PEA-OXA | mg 300.00 |
| Ultra-micronized PEA | mg 300.00 |
| Microcrystalline cellulose | mg 156.94 |
| Croscarmellose sodium | mg 90.00 |
| Polyvinylpyrrolidone | mg 20.00 |
| Magnesium stearate | mg 8.00 |
| Polysorbate 80 | mg 4.00 |
| Gastro-resistant coating based on macrogol 400, copolymer of the methacrylic acid-ethyl acrylate (1:1), polysorbate 80 | |

Example D

Tablets for Oral Use

Each tablet contains:

| | |
|---|---|
| PEA-OXA | mg 200.00 |
| Diacerein | mg 600.00 |
| Microcrystalline cellulose | mg 200.00 |
| Croscarmellose sodium | mg 120.00 |
| Polyvinylpyrrolidone | mg 30.00 |
| Magnesium stearate | mg 8.00 |
| Polysorbate 80 | mg 5.00 |
| Gastro-resistant coating based on macrogol 400, copolymer of the methacrylic acid-ethyl acrylate (1:1), polysorbate 80 | |

Example E

Tablets for Oral Use

Each tablet contains:

| | |
|---|---|
| PEA-OXLE | mg 100.00 |
| Ultra-micronized PEA | mg 500.00 |
| Microcrystalline cellulose | mg 156.94 |
| Croscarmellose sodium | mg 90.00 |
| Polyvinylpyrrolidone | mg 20.00 |
| Magnesium stearate | mg 8.00 |
| Polysorbate 80 | mg 4.00 |
| Gastro-resistant coating based on macrogol 400, copolymer of the methacrylic acid-ethyl acrylate (1:1), polysorbate 80 | |

Example F

Soft Gelatin Oil-Based Capsules

Each soft gelatin capsule contains:

| | | |
|---|---|---|
| PEA-OXA | mg | 300.00 |
| MEA-OXA | mg | 100.00 |
| Vegetable oil | mg | 400.00 |
| Soy lecithin | mg | 60.00 |
| Monostearate glyceryl | mg | 12.00 |
| Gastro-resistant coating based on macrogol 400, copolymer of the methacrylic acid-ethyl acrylate (1:1), polysorbate 80 | | |

Example G

Microgranules for Sublingual Use

A 1 g dosage of microgranules for sub-lingual absorption:

| | | |
|---|---|---|
| PEA-OXA | mg | 600.00 |
| Powder sorbitol | mg | 384.00 |
| Palmitate sucrose | mg | 13.00 |
| Polysorbate 80 (vegetable origin) | mg | 3.00 |

Example H

Bottles with Cap-Container for Oral Use

A 5 ml dose of sterile suspension, for paediatric use, in a bottle with pierceable cap-container, contains:

In the Pierceable Cap-Container:

| | | |
|---|---|---|
| PEA-OXA | mg | 50.00 |
| Lactose | mg | 50.00 |

In the Bottle:

| | | |
|---|---|---|
| Carboxymethylcellulose | mg | 25.00 |
| Bi-distilled water q.s. to | ml | 5.00 |

Example I

In-Mouth Disintegrable Microgranules for Oral Use

A 5 g dosage of in-mouth disintegrable microgranules, contains:

| | | |
|---|---|---|
| PEA-OXA | mg | 300.00 |
| Ultra-micronized PEA | mg | 150.00 |
| Luteolin | mg | 100.00 |
| Non-cariogenic sugar | mg | 200.00 |
| Pharmacologically acceptable excipients q.s. to | g | 5.00 |

Example L

Lyophilised Phials

Each 4 ml lyophilised phial contains:

| | | |
|---|---|---|
| PEA-OXA | mg | 50.00 |
| hydroxypropyl-β-cyclodextrin | mg | 500.00 |
| Manitol | mg | 80.00 |
| Polyvinylpyrrolidone | mg | 20.00 |

Each 3 ml solvent phial contains:

| | | |
|---|---|---|
| Na2HPO4 | mg | 4.0 |
| NaH2PO4 | mg | 1.12 |
| Bi-distilled water q.s. to | ml | 3.00 |

Example M

Eye-Drop

Each 5 ml eye-drop bottle, contains:

| | | |
|---|---|---|
| Ultra-micronized PEA | mg | 1.25 |
| PEA-OXA | mg | 1.25 |
| methyl-β-cyclodextrin | mg | 50.0 |
| Hyaluronic acid sodium salt | mg | 5.0 |
| Na2HPO4 | mg | 4.8 |
| NaH2PO4 | mg | 1.42 |
| NaCl | mg | 35.0 |
| Bi-distilled Water q.s. to | ml | 5.00 |

Example N

Soft Gelatin Oil-Based Capsules for Veterinary Use

Each soft gelatin capsule, for veterinary use (dog and cat), contains:

| | | |
|---|---|---|
| PEA-OXA | mg | 100.00 |
| Phosphatidylserine | mg | 50.00 |
| Resveratrol | mg | 60.00 |
| Oil-based excipients | mg | 300.00 |

Example O

Suppositories for Rectal Use

Each suppository contains:

| | | |
|---|---|---|
| PEA-OXA | mg | 200.00 |
| Saturated fatty acids triglycerides | mg | 1000.00 |

Example P

Cream for Dermatologic Use 100 g of cream contain:

| | | |
|---|---|---|
| PEA-OXA | g | 1.000 |
| Alpha tocopherol acetate | g | 4.000 |
| β-Cyclodextrin | g | 10.0 |
| Sodium hyaluronate | g | 0.040 |
| Hydrogenated castor oil (40)OE | g | 15.0 |
| Noveon AA1 | g | 0.160 |
| Bronopol | g | 0.005 |
| Flavour | g | 0.015 |
| Excipients and water q.s. to | g | 100 |

Example Q

Gel for Topical Oral Use 100 g of oral gel contain:

| | | |
|---|---|---|
| PEA-OXA | g | 0.500 |
| OEA-OXA | g | 0.500 |
| Glycerol | g | 10.000 |
| β-Cyclodextrin | g | 5.000 |
| Sodium alginate | g | 2.500 |
| Sodium hyaluronate | g | 0.040 |
| Bronopol | g | 0.050 |
| Triclosan | g | 0.300 |
| Distilled water q.s. to | g | 100.00 |

Example R

Vaginal Gel 100 g of vaginal gel contain:

| | | |
|---|---|---|
| PEA-OXA | g | 1.000 |
| SEA-OXA | g | 1.000 |
| 2-phenylethanol | g | 0.150 |
| Glycerol | g | 10.000 |
| β-Cyclodextrin | g | 5.000 |
| Hydrogenated castor oil (40) OE | g | 1.000 |
| Methyl-p-oxybenzoate | g | 0.100 |
| Noveon AA1 | g | 1.000 |
| Sodium hyaluronate | g | 0.080 |
| Flavour | g | 0.200 |
| Distilled water q.s. to | g | 100.00 |

Example S

Bottles for Intravesical Instillation

Each 50 ml sterile bottle contains:

| | | |
|---|---|---|
| PEA-OXA | mg | 300.00 |
| Adelmidrol | mg | 1000.00 |
| β-Cyclodextrin | g | 3.000 |
| Hyaluronic acid | mg | 500.00 |
| Sterile bi-distilled water q.s. to | ml | 50.00 |

Example T

Bottle for Intravenous Administration

Each 500 ml sterile bottle contains:

| | | |
|---|---|---|
| PEA-OXA | mg | 500 |
| Soy lipids | g | 50.0 |
| Egg phospholipids | g | 6.0 |
| Sterile bi-distilled water q.s. to | ml | 500.0 |

The invention claimed is:

1. A compound of general formula (I):

$$R-\underset{N}{\overset{X}{\underset{}{\bigtriangleup}}}Y \quad (I)$$

enantiomers, diastereoisomers, racemes and mixtures, salts, thereof,
selected from the group consisting of:
2-pentadecyl-2-oxazoline,
2-heptadecyl-2-oxazoline,
2-tridecyl-2-oxazoline,
2-(8-heptadecenyl)-2-oxazoline, and
2-pentadecyl-2-oxazole.

2. A compound according to claim 1, for use as an inhibitory modulator of the activity of the FAAH and NAAA enzymes.

3. A compound according to claim 1, for use as an anti-inflammatory.

4. Pharmaceutical composition comprising one or more compounds of formula (I) according to claim 1 together with pharmaceutically acceptable excipients.

5. Pharmaceutical composition according to claim 4, wherein said pharmaceutical composition is for oral, parenteral or topical administration.

6. A compound of formula (I) according to claim 1, for use in association with one or more different compounds of formula (I), for a combined, separate or sequential administration.

7. A compound of formula (I) according to claim 1, for use in association with palmitoylethanolamide, for a combined, separate or sequential administration.

* * * * *